United States Patent
Fujisawa et al.

(10) Patent No.: US 7,838,829 B2
(45) Date of Patent: Nov. 23, 2010

(54) CHARGED PARTICLE BEAM DEVICE

(75) Inventors: Akiko Fujisawa, Hitachinaka (JP); Eiko Nakazawa, Mito (JP); Isao Nagaoki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 322 days.

(21) Appl. No.: 12/046,159

(22) Filed: Mar. 11, 2008

(65) Prior Publication Data

US 2008/0224037 A1 Sep. 18, 2008

(30) Foreign Application Priority Data

Mar. 12, 2007 (JP) .............................. 2007-062424

(51) Int. Cl.
*G01N 23/00* (2006.01)
(52) U.S. Cl. ..................... 250/307; 250/306; 250/310; 250/311; 382/141; 382/144; 382/145; 382/149; 382/169; 348/80
(58) Field of Classification Search ................. 250/306, 250/307, 310, 311; 382/141, 144, 145, 149, 382/168, 169; 348/80
See application file for complete search history.

(56) References Cited

U.S. PATENT DOCUMENTS

| | | | | |
|---|---|---|---|---|
| 6,878,934 B2* | 4/2005 | Inada et al. | ................. | 250/307 |
| 7,022,989 B2* | 4/2006 | Inada et al. | ................. | 250/311 |
| 7,145,156 B2* | 12/2006 | Abe | ................. | 250/492.2 |
| 2001/0021269 A1* | 9/2001 | Inoue | ................. | 382/169 |
| 2002/0027199 A1* | 3/2002 | Inada et al. | ................. | 250/311 |

FOREIGN PATENT DOCUMENTS

| | | |
|---|---|---|
| JP | 10-92354 A | 4/1998 |
| JP | 2001-148230 A | 5/2001 |
| JP | 2004-253261 A | 9/2004 |
| JP | 2006-228748 A | 8/2006 |

OTHER PUBLICATIONS

Japanese Office Action dated Mar. 31, 2009 (Six (6) pages).

* cited by examiner

*Primary Examiner*—Jack I Berman
*Assistant Examiner*—Michael Maskell
(74) *Attorney, Agent, or Firm*—Crowell & Moring LLP

(57) ABSTRACT

There is provided a charged particle beam device which can prevent a specimen from not being able to be observed due to entering of a part of a grid of a mesh in a field of view, each pixel of a scanning transmission electron microscope image is displayed on the basis of a gray value of a predetermined gradation scale. In the case where the number of pixels of a predetermined gray value is less than a predetermined percentage, it is decided that a mesh image is not included in the scanning transmission electron microscope image. In the case where the number of pixels of the predetermined gray value is not less than a predetermined percentage, it is judged that the mesh image is included in the scanning transmission electron microscope image. In the case where the mesh image is included in the scanning transmission electron microscope image, a magnification is increased, a specimen stage is moved, or beam deflection is performed, and when the mesh image is not anymore included in the scanning transmission electron microscope image, the predetermined gradation scale is converted to other gradation scale and a scanning transmission electron microscope image is obtained.

7 Claims, 6 Drawing Sheets

FIG. 2A
FIG. 2B
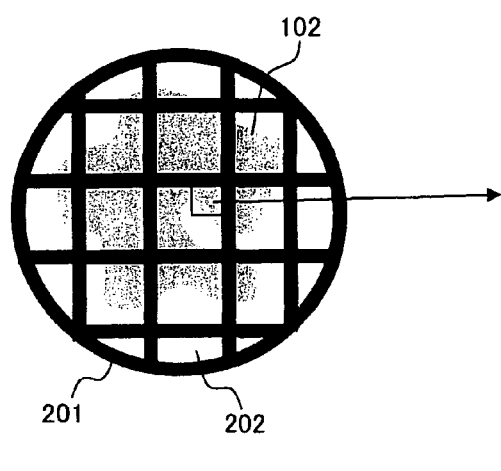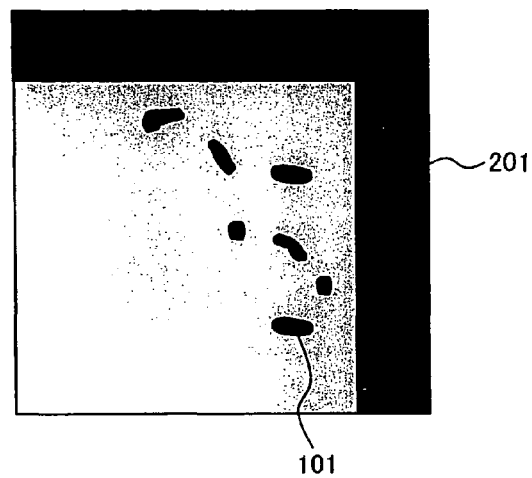
FIG. 3A
FIG. 3B
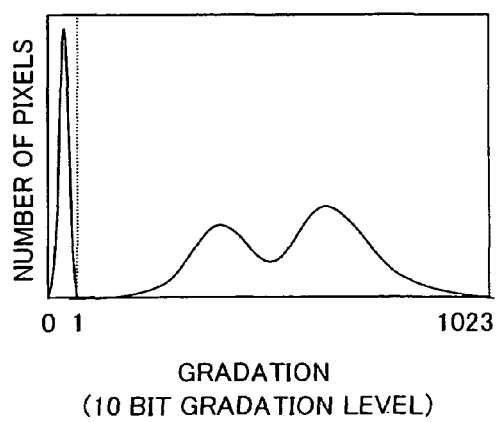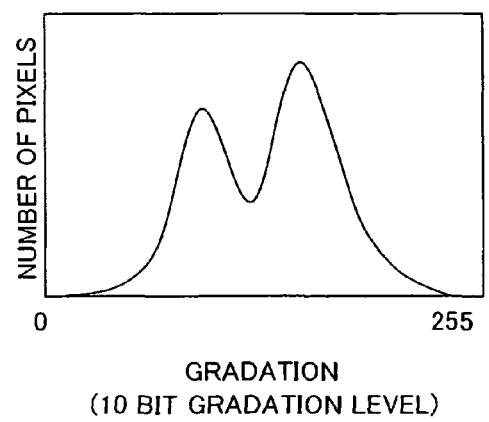

CHARGED PARTICLE BEAM DEVICE

BACKGROUND OF THE INVENTION

1. Field of the Invention

The present invention relates to charged particle beam devices for obtaining scanning transmission electron microscope images and, more particularly, relates to a charged particle beam device which uses a mesh which is for holding a specimen.

2. Description of the Related Art

A scanning transmission electron microscopy uses a mesh which is for holding a specimen. Therefore, in the case of observing an objective specimen by automatically moving a field of view, there is a case where a part of a grid of the mesh is entered in the field of view. When the grid of the mesh is entered in the field of view, there is a case where the specimen is lost to view in a monitor because the specimen and the grid are extremely different in shade level.

Japanese Patent Application Laid-Open No. 2006-228748 proposes a method which automatically determines whether or not an automatically photographed field of view is a field of view which is suitable for search of an objective morphology, and in the case where it is not suitable for observation and search, movement to the next field of view is made.

In the method disclosed in Japanese Patent Application Laid-Open No. 2006-228748, work for determining whether or not the field of view is suitable or not is complicated.

SUMMARY OF THE INVENTION

An object of the present invention is to provide means which can prevent a specimen from not being able to be observed due to entering of a part of a grid of a mesh in a field of view in a charged particle beam device which uses a mesh which is for holding the specimen.

According to a scanning transmission charged particle beam device of the present invention, each pixel of a scanning transmission electron microscope image is displayed on the basis of a gray value of a predetermined gradation scale. In the case where the number of pixels of a predetermined gray value is less than a predetermined percentage, it is determined that a mesh image is not included in the scanning transmission electron microscope image, and in the case where the number of pixels of the predetermined gray value is not less than the predetermined percentage, it is determined that the mesh image is included in the scanning transmission electron microscope image.

In the case where the mesh image is not included in the scanning transmission electron microscope image, the predetermined gradation scale is converted to other gradation scale and a scanning transmission electron microscope image is obtained. In the case where the mesh image is included in the scanning transmission electron microscope image, a magnification is increased, a specimen stage is moved, or beam deflection is performed, and when the mesh image is not anymore included in the scanning transmission electron microscope image, the predetermined gradation scale is converted to other gradation scale and a scanning transmission electron microscope image is obtained.

According to the present invention, it is possible to prevent a specimen from not being able to be observed due to entering of a part of a grid of a mesh in a field of view in a charged particle beam device which uses a mesh which is for holding the specimen.

BRIEF DESCRIPTION OF THE DRAWINGS

FIGS. 2A and 2B are views for explaining examples of a mesh in the case where a field of view is searched or in the case where a specimen image is observed by the scanning transmission electron microscopy according to the present invention;

FIGS. 3A and 3B are views showing histograms of scanning transmission electron microscope images displayed in a monitor by the scanning transmission electron microscopy according to the present invention;

DESCRIPTION OF REFERENCE NUMERALS

Figure 1:
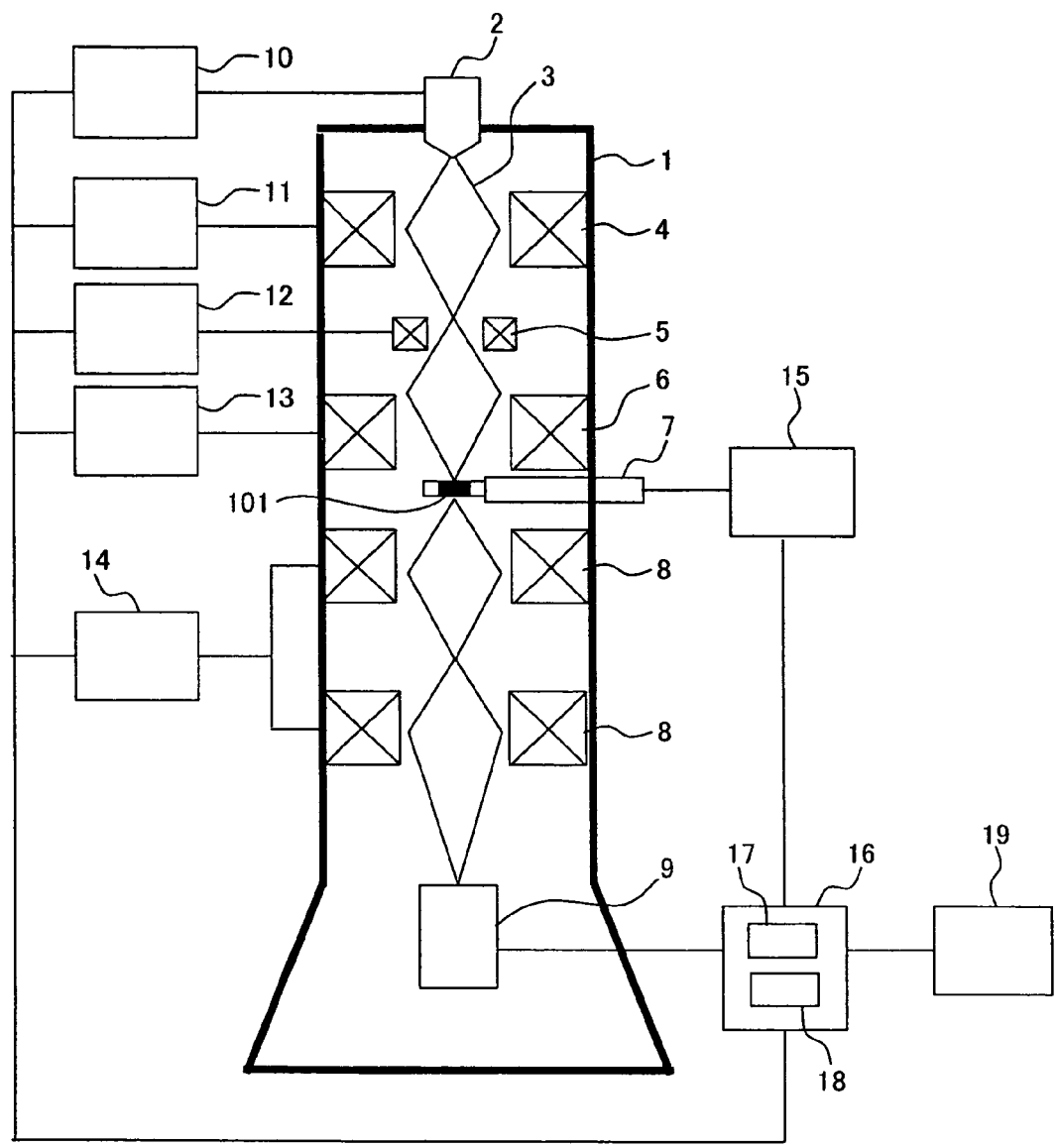
FIG. 1 is a schematic diagram of an electron microscopy showing an example of a configuration of a scanning transmission electron microscopy according to the present invention.

1 Electron microscopy body
2 Electron gun
3 Electron beam
4 Irradiation lens
5 Scanning coil
6 Objective lens
7 Specimen stage
8 Magnifying lens system
9 Imaging device
10 Electron gun control device
11 Irradiation lens control device
12 Scanning coil control device
13 Objective lens control device
14 Magnifying lens system control device
15 Specimen stage control device
16 Computing machine mounted with control device and image processing control device
17 Control device
18 Image processing control device
19 Monitor
101 Specimen

DESCRIPTION OF THE PREFERRED EMBODIMENTS

A charged particle beam device according to the present invention will be described hereinafter in detail with reference to the drawings. The charged particle beam device of the present invention includes a transmission electron microscopy and a scanning transmission electron microscopy. In what follows, the scanning transmission electron microscopy will be described as an example of the present invention, however, the present invention is also applicable to the transmission electron microscopy.

A structure of the scanning transmission electron microscopy of this example will be described with reference to FIG. 1. The scanning transmission electron microscopy of this example includes an electron gun 2, an irradiation lens 4, a scanning coil 5, an objective lens 6, a specimen stage 7, a magnifying lens system 8, and an imaging device 9, and these are provided in an electron microscopy body 1. The imaging device 9 may be provided with a scintillator and a digital camera (charge coupled device (CCD) camera), for example.

The scanning transmission electron microscopy of this example further includes an electron gun control device 10 which controls the electron gun 2, an irradiation lens control device 11 which controls the irradiation lens 4, a scanning coil control device 12 which controls the scanning coil 5, an objective lens control device 13 which controls the objective lens 6, a magnifying lens control device 14 which controls the magnifying lens system 8, a specimen stage control device 15 which controls the specimen stage 7, a computer 16, and a monitor 19. The computer 16 includes a control device 17 and an image processing control device 18. The control device 17 controls the electron gun control device 10, the irradiation lens control device 11, the scanning coil control device 12, the objective lens control device 13, the magnifying lens control device 14, and the specimen stage control device 15.

Electron beams 3 emitted from the electron gun 2 are converged by the irradiation lens 4, and are deflected by the scanning coil 5 composed of deflection coils of an X direction and a Y direction. The electron beams 3 deflected in two directions are focused on a specimen 101 which is held by the specimen stage 7, by the objective lens 6, and are scanned on a specimen plane. The electron beams 3 transmitted through the specimen 101 are enlarged by the magnifying lens system 8, and imaged by the imaging device 9. A scanning transmission electron microscope image (STEM image) from the imaging device 9 is sent to the computer 16.

The image processing control device 18 displays the scanning transmission electron microscope image from the imaging device 9 in the monitor 19. At this time, the image processing control device 18 reads a gray value of each pixel of the scanning transmission electron microscope image, produces a histogram in which a horizontal axis indicates the gray value and a vertical axis indicates the number of pixels, and displays the same in the monitor 19. Examples of the histograms will be described later with reference to FIGS. 3A and 3B.

The mesh for use in the case where a field of view is searched or in the case where a specimen image is observed will be described with reference to FIGS. 2A and 2B. As shown in FIG. 2A, the mesh includes a metal net-like grid 201 and a support membrane 202. FIG. 2A shows a state where a solution 102 including a specimen to be observed is on the mesh. FIG. 2B shows an enlarged image of the neighborhood of the mesh. As shown in the drawing, in the case of observing by applying negative dyeing to the specimen 101 such as a virus, there are many that the specimen 101 is gathered in the vicinity of the mesh due to surface tension of a dyeing agent. Therefore, when the specimen 101 is observed, a part of the grid 201 of the mesh is entered in a field of view. There is a case where the specimen 101 is not displayed in a monitor because the specimen and the grid 201 of the mesh are extremely different in shade.

FIGS. 3A and 3B show the examples of the histograms to be displayed in the monitor 19. The horizontal axis of the histogram shows a gradation of a gray value of the scanning transmission electron microscope image, and the vertical axis shows the number of pixels of the gray value of the scanning transmission electron microscope image. The gradation of the gray value of the scanning transmission electron microscope image in the horizontal axis is usually displayed in not less than 10 bits. In the case where the gradation is displayed in 10 bits as this example, the gray value is divided into 1024 gradation levels from the minimum value 0 to the maximum value 1023, the left end shows the darkest value 0, and the right end shows the brightest value 1023.

FIG. 3A shows an example of the histogram in the case where a part of the mesh is displayed in the field of view. When there is the part of the grid of the mesh in the field of view, the number of pixels of the gray value 0 increases in the histogram. That is, having many of the gray value 0 is a sign that represents an image of the grid of the mesh.

FIG. 3B shows a histogram after that data of the gray value 0 is removed and an image at portions whose gray values are 1 to 1023 is converted to 256 gradation levels by use of the image processing control device 18. This histogram represents an image in which the image of the grid of the mesh is removed.

Figure 4:
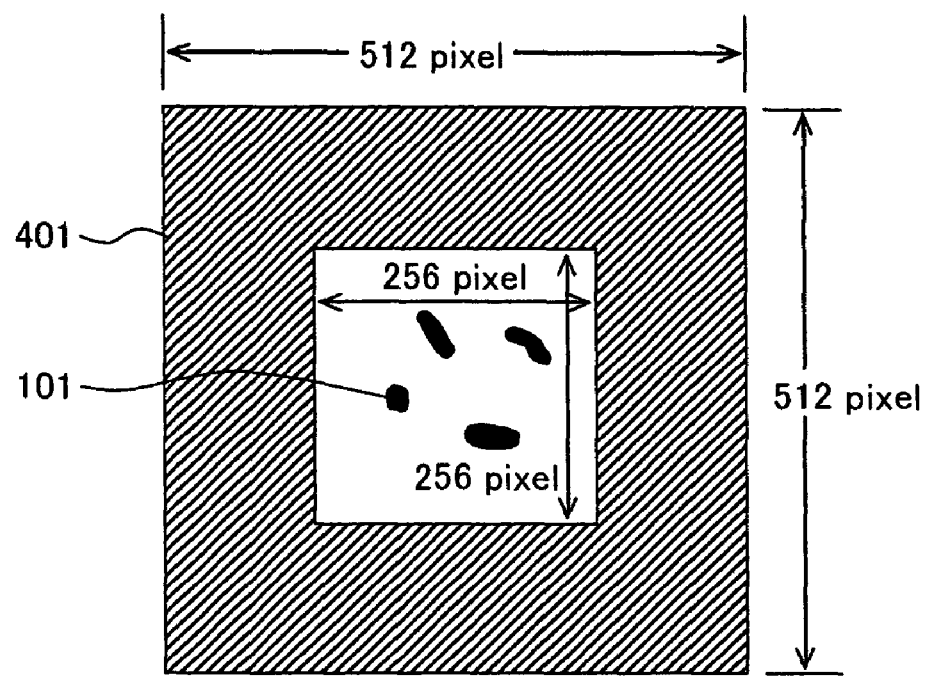
FIG. 4 is a view for explaining a method for setting a monitoring region in the scanning transmission electron microscopy of this example.

A method for setting a monitoring region in the scanning transmission electron microscopy of this example will be described with reference to FIG. 4. According to this example, as shown in the drawing, an annular portion 401 shown by hatched line excluding 256×256 pixels at the central portion in the scanning transmission electron microscope image of 512×512 pixels is set as the monitoring region. In this case, the monitoring region is a region where the number of pixels of the gray value 0 in the scanning transmission electron microscope image is calculated. The gray value 0 represents an image of the grid of the mesh. As to be described hereinafter, a percentage of the gray value 0 included in the monitoring region is calculated, and from its result, it is determined whether or not the image of the grid of the mesh is included in the scanning transmission electron microscope image.

The monitoring region shown in this case is a mere example, for example, in the scanning transmission electron microscope image of 512×512 pixels, a portion excluding 384×384 pixels at the central portion may be set as the monitoring region.

Methods for removing a mesh portion from the scanning transmission electron microscope image and converting the image from 1024 to 256 gradation levels in the image processing control device 18 will be described with reference to FIGS. 5 to 7.

A first example of the method for removing the mesh portion from the scanning transmission electron microscope image and converting the image from 1024 to 256 gradation levels in the image processing control device 18 of the scanning transmission electron microscopy of this example will be described with reference to FIG. 5.

In step S101, an operator prepares the specimen 101 to be an observing object, operates the scanning transmission electron microscopy, and sets a search range which is for automatically moving a field of view.

In step S102, movement to the field of view set up is automatically made by the specimen stage 7, a transmissive electron is detected by the imaging device 9, and the scanning transmission electron microscope image is obtained by the image processing control device 18.

In step S103, the image processing control device 18 calculates how many percent of the number of pixels of the gray value 0 is occupied in the monitoring region of the scanning transmission electron microscope image.

In step S104, it is determined whether or not the number of pixels of the gray value 0 is not less than 5% in the monitoring region. In the case that the number of pixels of the gray value 0 is not less than 5%, it is judged that an image of the grid of the mesh is included in the monitoring region, and the process proceeds to step S105. In the case that the number of pixels of the gray value 0 is less than 5%, it is judged that the image of the grid of the mesh is not included in the monitoring region, and the process proceeds to step S106.

In step S105, a portion of the image whose gray values are 1 to 1023 is converted to 256 gradation levels. That is, the portion is converted to the image of 256 gradation levels after a portion of the gray value 0 being removed. In step S106, the image is directly converted from 1024 to 256 gradation levels. That is, the portion of all the gray values 0 to 1023 is converted to 256 gradation levels. In step S107, the image converted to 256 gradation levels and its histogram are displayed in the monitor 19.

A second example of the method for removing the mesh portion from the scanning transmission electron microscope image and converting the image from 1024 to 256 gradation levels in the image processing control device 18 of the scanning transmission electron microscopy of this example will be described with reference to FIG. 6.

Figure 5:
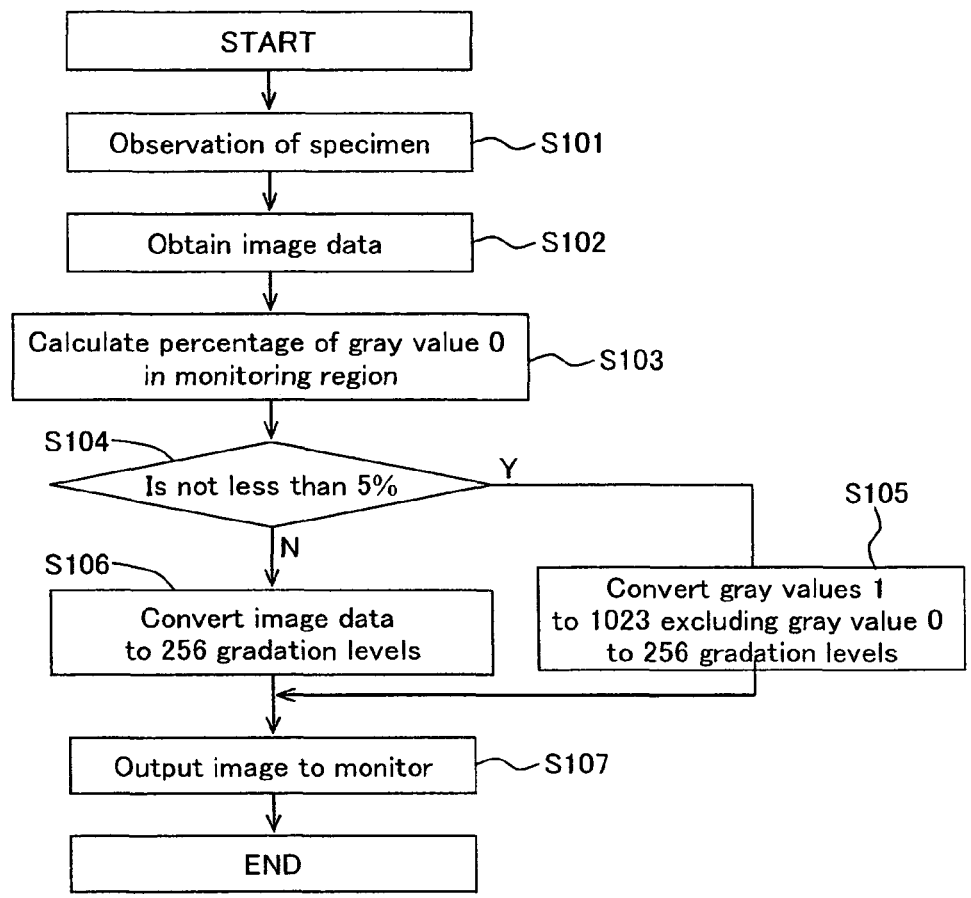
FIG. 5 is a flow chart for explaining a first example of a method for converting from 1024 to 256 gradation levels in the scanning transmission electron microscopy of example.

Steps S201 to S204 are the same as steps S101 to S104 shown in FIG. 5. In this case, a portion different from the example of FIG. 5 will be described.

In step S204, it is determined whether or not the number of pixels of the gray value 0 is not less than 5% in the monitoring region. In the case that the number of pixels of the gray value 0 is not less than 5%, it is judged that an image of the grid of the mesh is included in the monitoring region, and the process proceeds to step S205. In the case that the number of pixels of the gray value 0 is less than 5%, it is judged that the image of the grid of the mesh is not included in the monitoring region, and the process proceeds to step S206.

In step S205, the scanning coil control device 12 is controlled by the control device 17, and a magnification is increased by one level, thus, a smaller region on the specimen is displayed. Accordingly, the image of the grid of the mesh can be removed from a field of view. Such magnification change is repeated till the number of pixels of the gray value 0 becomes less than 5% in the monitoring region. In the monitoring region, when the number of pixels of the gray value 0 becomes less than 5%, the process proceeds to step S206.

Steps S206 and step S207 are the same as steps S106 and S107 of the example shown in FIG. 5. That is, the image is converted from 1024 to 256 gradation levels in step S206. In step S207, the image converted to 256 gradation levels and its histogram are displayed in the monitor 19.

A third example of the method for removing the mesh portion from the scanning transmission electron microscope image and converting the image from 1024 to 256 gradation levels in the image processing control device 18 of the scanning transmission electron microscopy of this example will be described with reference to FIG. 7.

Figure 6:
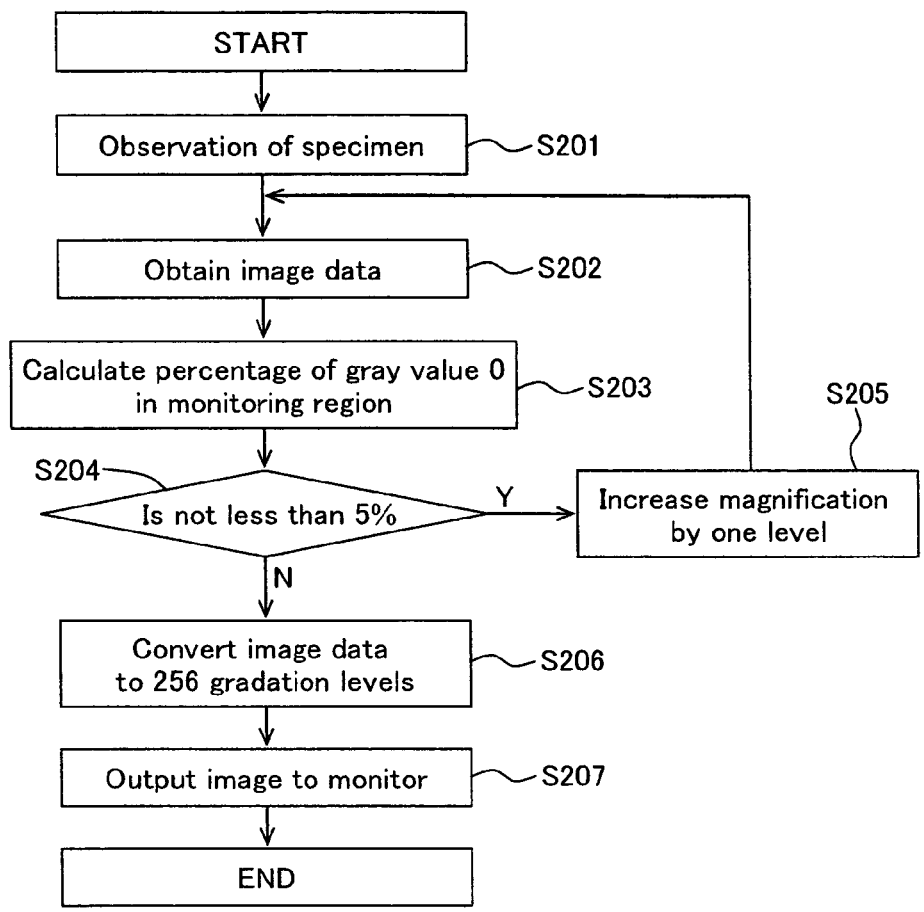
FIG. 6 is a flow chart for explaining a second example of a method for converting from 1024 to 256 gradation levels in the scanning transmission electron microscopy of this example.

Steps S301 to step S304, step S306, and step S307 are the same as steps S201 to S204, step S206, and step S207 of the example shown in FIG. 6. In this example, the process of step S305 is different from that of step S205 of the example shown in FIG. 6. In this case, step S305 will be described.

In step S305, the specimen stage control device 15 is controlled by the control device 17, and the specimen stage 7 is moved to an X direction and a Y direction. Thus, by moving the specimen stage 7, a field of view is changed and the image of the grid of the mesh can be removed from the field of view. In addition, in order to change the field of view, beams may be moved to the X direction and the Y direction by controlling the scanning coil control device 12 in place of moving the specimen stage 7.

Such movement of the field of view is repeated till the number of pixels of the gray value 0 becomes less than 5% in the monitoring region.

In the case where the number of pixels of the gray value 0 in the monitoring region tends to be increased by the movement of the field of view, a moving direction and an amount of movement are set so that the moving direction and the amount of movement of the specimen stage reduce as compared with previous values. When the number of pixels of the gray value 0 becomes less than 5% in the monitoring region, the process proceeds to step S306.

Figure 7:
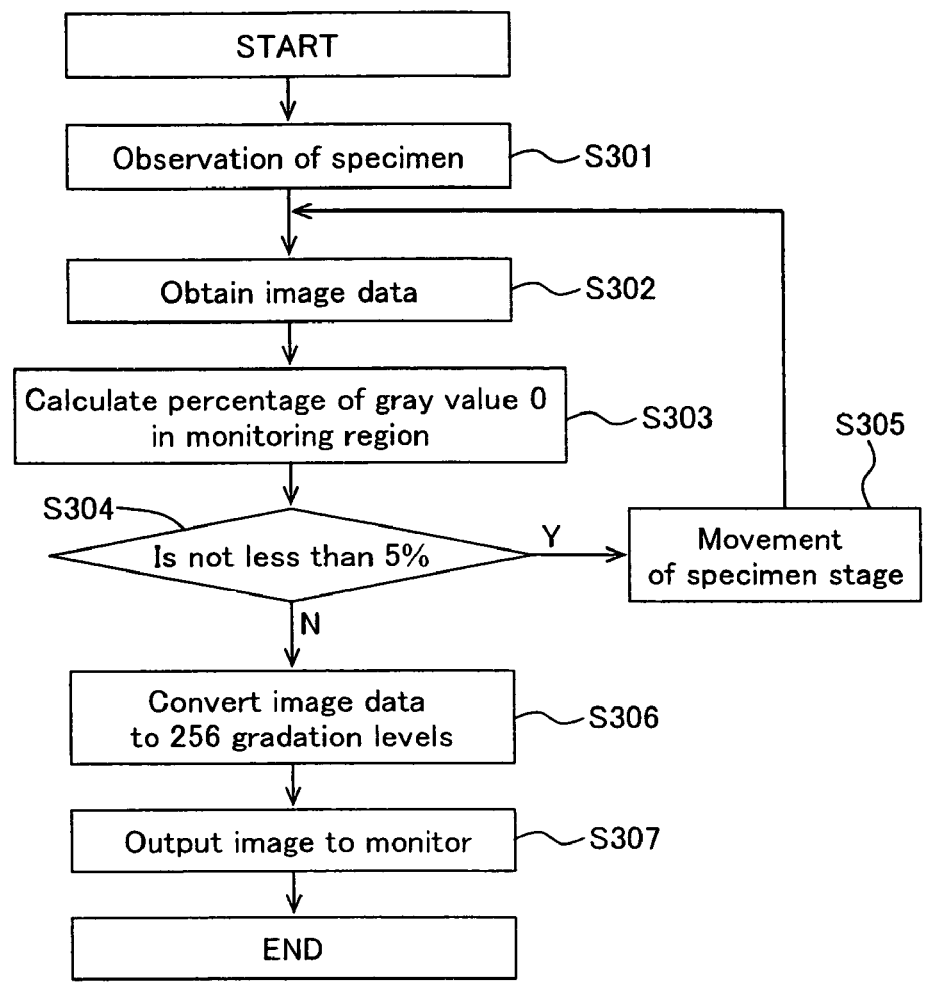
FIG. 7 is a flow chart for explaining a third example of a method for converting from 1024 to 256 gradation levels in the scanning transmission electron microscopy of this example.

The monitoring region is used in the examples shown in FIGS. 5 to 7. That is, in steps S104, S204, and S304, it is determined whether or not the number of pixels of the gray value 0 is not less than 5% in the monitoring region. However, the present invention does not have to use the monitoring region. That is, in steps S104, S204, and S304, it may be determined whether or not the number of pixels of the gray value 0 is not less than 5% in the scanning transmission electron microscope image obtained by the imaging device in place of the monitoring region.

Further, a percentage of the number of pixels of the gray value 0 is determined in steps S104, S204, and S304 in the examples shown in FIGS. 5 to 7. However, a percentage in which the gray values are predetermined numbers, for example, a percentage of the number of pixels of the gray values 0 and 1 may be calculated. Further, as a reference for determination it is not less than 5%, however, this is a mere example, it may be not less than 6%, or it may be not less than 7%.

As described above, examples of the present invention have been described, however, the present invention is not limited to the above described examples, but, it is to be easily understood to those skilled in the art that the present invention can be applicable to various changes in the scope of the present invention as set forth in the appended claims.

What is claimed is:

1. A method for obtaining a transmission electron microscope image, the method comprising:
    attaching a mesh, which holds a specimen, to a specimen stage;
    emitting a charged particle beam from an electron gun;
    detecting said charged particle beam passing through the specimen by an imaging device;
    obtaining a transmission electron microscope image by the imaging device;
    in the case where a number of pixels having a gray value indicating a grid of said mesh is not less than a predetermined percentage of a number of pixels of a monitoring region, removing pixel data having said predetermined gray value, converting the gradation scale to an other gradation scale and obtaining a transmission electron microscope image; and
    displaying the transmission electron microscope image in a monitor.

2. The method for obtaining the transmission electron microscope image according to claim 1, wherein:
    when the number of pixels having said gray value is not less than a predetermined percentage of the number of pixels of the monitoring region, it is determined that the mesh image is included in the monitoring region; and
    when the number of pixels having said gray value is less than the predetermined percentage of the number of pixels of the monitoring region, it is determined that the mesh image is not included in the monitoring region.

3. The method for obtaining the transmission electron microscope image according to claim 2, wherein, when the mesh image is determined to be included in the monitoring region, a magnification is increased, whereby, when the mesh image is not anymore included in the transmission electron microscope image, the gradation scale is converted to said other gradation scale, and a transmission electron microscope image is obtained.

4. The method for obtaining the transmission electron microscope image according to claim 2, wherein, when the mesh image is determined to be included in the monitoring region, the specimen stage is moved, whereby, when the mesh image is not anymore included in the transmission electron microscope image, the gradation scale is converted to said other gradation scale, and a transmission electron microscope image is obtained.

5. The method for obtaining the transmission electron microscope image according to claim 2, wherein, when the mesh image is determined to be included in the monitoring region, beam deflection is performed, whereby, when the mesh image is not anymore included in the transmission electron microscope image, the gradation scale is converted to said other gradation scale, and a transmission electron microscope image is obtained.

6. A method for obtaining a transmission electron microscope image, the method comprising:
   attaching a mesh, which holds a specimen, to a specimen stage;
   emitting a charged particle beam from an electron gun;
   detecting charged particle beam passing through the specimen by an imaging device;
   obtaining a transmission electron microscope image by the imaging device;
   in the case where a number of pixels having a gray value 0 is not less than a predetermined percentage of a number of pixels of a monitoring region, removing pixel data having said gray value, converting a gradation scale to an other gradation scale, and obtaining a transmission electron microscope image; and
   displaying the transmission electron microscope image in a monitor.

7. The method for obtaining the transmission electron microscope image according to claim 6, wherein:
   when the number of pixels having said gray value is not less than a predetermined percentage of the number of pixels of the monitoring region, it is determined that the mesh image is included in the monitoring region; and
   when the number having said gray value is less than the predetermined percentage of the number of pixels of the monitoring region it is determined that the mesh image is not included in the monitoring region.

* * * * *